(12) United States Patent
Xin et al.

(10) Patent No.: US 6,656,717 B1
(45) Date of Patent: Dec. 2, 2003

(54) CYCLIC AMP PHOSPHODIESTERASE ISOFORMS AND METHODS OF USE

(75) Inventors: Xiaonan Xin, West Hartford, CT (US); Axel Unterbeck, Madison, CT (US); Yinghe Hu, San Diego, CA (US)

(73) Assignee: Memory Pharmaceuticals Corp., Montvalle, NJ (US)

( * ) Notice: Subject to any disclaimer, the term of this patent is extended or adjusted under 35 U.S.C. 154(b) by 0 days.

(21) Appl. No.: 09/602,735

(22) Filed: Jun. 23, 2000

Related U.S. Application Data
(60) Provisional application No. 60/141,196, filed on Jun. 25, 1999.

(51) Int. Cl.$^7$ .............................. C12N 9/14; C12N 9/64; C08G 63/66; C08G 69/26
(52) U.S. Cl. ...................... 435/195; 435/226; 530/300; 530/350
(58) Field of Search ................................ 435/195, 226; 536/23.1; 530/300, 350

(56) References Cited

PUBLICATIONS

Braun R. P. et al, Sequence of the hexametric juvenile hormone–binding protein from the hemolymph of *Locusta migratoria*, J. Biol. Chem. 1996, 271, 31756–31762.*

Graeme B. Bolger, "The Multienzyme PDE4 Cyclic Adenosine Monophosphate–Specific Phosphodiesterase Family: Intracellular Targeting, Regulation, and Selective Inhibition by Compounds Exerting . . . ", Advances in Pharmacology, vol. 44, (1998).

Bolger, et al., "Characterization of five different proteins produced by alternatively spliced mRNAs from the human cAMP–specific phosphodiesterase PDE4D gene," Bio Chem, pp. 539–548 (1997).

Nemoz, et al., "Identification of cyclic AMP–phosphodiesterase variants from the PDE4D gene expressed in human peripheral mononuclear cells," FEBS Letter 384, (1996).

Monaco, et al., "Structure of Two Rat Genes Coding for Closely Related Rolipram–sensitive cAMP Phosphodiesterases," The Journal of Biological Chemistry, vol. 269 (1994).

Bolger, et al., "Differential CNS expression of alternative mRNA isoforms of the mammalian genes encoding cAMP–specific phosphodiesterases," (1994).

* cited by examiner

*Primary Examiner*—Nashaat T. Nashed
*Assistant Examiner*—Malgorzata Walicka
(74) *Attorney, Agent, or Firm*—Millen, White, Zelano & Branigan, P.C.

(57) ABSTRACT

Human and rat cAMP phosphodiesterase isoforms (denoted PDE4Ds), as well as the DNA (RNA) encoding such polypeptides, are disclosed. Also disclosed are methods for utilizing such polypeptides in diagnostic assays for identifying mutations in nucleic acid sequences encoding the polypeptides of the present invention, for detecting altered levels of the polypeptide of the present invention as a means of detecting diseases and methods of screening potential modulators, especially inhibitors, of the novel PDE4Ds (denoted PDE4D6) disclosed herein as a means of increasing cyclic AMP in neurons and thus treating neurological problems, such as long term memory loss, if not preventing such maladies entirely. Transgenic animals expressing polypeptides disclosed herein are also described.

10 Claims, 3 Drawing Sheets

CYCLIC AMP PHOSPHODIESTERASE ISOFORMS AND METHODS OF USE

This application claims priority of U.S. Provisional Application Serial No. 60/141,196, filed Jun. 25, 1999, the disclosure of which is hereby incorporated by reference in its entirety.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are cAMP (cyclic adenosine 5'-monophosphate) phosphodiesterases, and fragments thereof derived from mammals, especially humans, rats, and mice, and most especially from the brains, for example, the hippocampal and other memory related regions. Both human and rat isoforms are specifically disclosed herein. The methods according to the present invention disclose uses of this polypeptide in diagnostic assays and for screening potential therapeutic agents, as well as other potential uses.

The phosphodiesterases (PDEs) represent a family of enzymes that catalyze the hydrolysis of the various cyclic nucleoside monophosphates (including cAMP). These cyclic nucleotides have been found to act as second messengers within the cells, which messengers carry impulses from cell surface receptors having bound various hormones and neurotransmitters. The job of phosphodiesterases is to degrade these cyclic mononucleotides once their messenger role is completed (thereby regulating the level of cyclic nucleotides within the cells and maintaining cyclic nucleotide homeostasis).

A number of different families of such phosphodiesterases have been identified, with the predominant family having been designated PDE4, as distinguished by various kinetic properties (such as low Michaelis constant for cAMP and sensitivity to certain drugs). [See: Wang et al., Expression, Purification, and Characterization of human cAMP-Specific Phosphodiesterase (PDE4) Subtypes A, B, C, and D, *Biochem. Biophys. Res. Comm.*, 234, 320–324 (1997)] Since the PDEs have been found to possess distinct biochemical properties it is likely that they are subject to a variety of different forms of regulation.

The phosphodiesterases disclosed according to the present invention exist in mammals in the form of isoenzymes (which represent different molecular forms of the same enzyme polypeptide). These phosphodiesterases (denoted PDE4D) are localized in the cytosol of the cell and are unassociated with any known membranous structures. The PDE4D isoenzymes specifically degrade cAMP and are a common target for such pharmacological agents as antidepressants (for example, rolipram). Also, inhibitors of PDE4 isoenzymes are powerful anti-inflammatory agents and may also be useful as anti-asthmatics.

In the past, attempts at isolation of such proteins have proven difficult since they are commonly present at very low concentration and have shown a tendency toward instability on purification. [See: Salanova et al., Heterologous Expression and Purification of Recombinant Rolipram-Sensitive Cyclic AMP-Specific Phosphodiesterases, Methods: *A Companion to Methods in Enzymology* 14, 55–64 (1998)]

Cloning of the isoenzymes of PDE4 have shown that mammals have up to 4 genes for PDE4, and this is true of rats, mice and humans. Further, each such gene has been found to code for several different protein variants. Thus, each PDE4 gene has been found to code for at least 2 or more polypeptides. The physiological roles for this plethora of forms of PDE4 is beginning to be understood with the advent of Recombinant DNA technology and the use of cDNAs to clone the various polypeptide forms of these enzymes. Such methodology is essential to the successful screening of drugs having, for example, anti-inflammatory activity.

BRIEF SUMMARY OF THE INVENTION

The present invention is directed to novel polypeptides, with or without associated phosphodiesterase activity, and containing a novel amino acid sequence as part of the overall sequence. The present invention is also directed to novel cDNA clones coding for such polypeptides and sequences of DNA contained within the genome and which may code for such novel polypeptide sequences.

The present invention is also directed to novel cells and cell lines containing polynucleotides that make them capable of expressing the novel polypeptides disclosed herein.

It is one object of the present invention to provide methods of forming such cell lines by incorporating novel DNA sequences of the invention in vectors that can be used to transform cells into cells that express the polypeptides containing the novel sequences disclosed herein. Such polypeptides will often have phosphodiesterase activity that will affect the level of cAMP within the transformed cells so that the cAMP level will provide an indicator of the level of phosphodiesterase within such cells.

It is a further object of the present invention to provide such vectors, containing the novel DNAs disclosed herein, and genetically transformed cells capable of expressing the polypeptides coded for by said novel DNAs.

In the brain, the level of cAMP within neurons is believed to be related to the quality of memory, especially long term memory. Thus, since PDE4D degrades cAMP, the level of this enzyme could have effects on memory in animals, for example, in humans.

It is therefore another object of the present invention to monitor the levels of the novel polypeptides disclosed herein as a means of determining the presence of a disease condition or susceptibility to such condition, especially where such condition involves loss of memory, most especially long term memory.

It is a still further object of the present invention to provide novel DNA sequences present in cells, especially brain cells, that can serve as the target for probes capable of disclosing the presence of a mutation in said novel DNA sequences, whereby the presence of such a mutation indicates a possible cause for over- or under-activity of a novel phosphodiesterase as disclosed herein.

It is also a further object of the present invention to provide a method of using the transformed cells disclosed herein as a means of screening potential chemical agents, either small molecules or otherwise, for ability to inhibit the actions of phosphodiesterase polypeptides disclosed herein and thereby provide novel therapeutic agents for the treatment of diseases, for example, impairment of memory, especially long term memory, or as prophylactic agents to be used in anticipation of such conditions, perhaps as secondary conditions incident to already existing diseases.

Finally, it is an additional object of the present invention to provide transgenic animals, especially transgenic mice, into whose genome has been inserted a gene, present as one or more copies thereof, coding for the human isoform of the PDE4D6 of the invention, especially where this gene replaces the mouse gene otherwise coding for any corresponding isoform, and most especially where the effect of such humanization is the overproduction of the human PDE4D6 isoform in said mouse. The invention also relates to the production of "knock-out" animals, especially "knock-out" mice, whose genes for PDE4D6 isoforms have been rendered non-functional so that said mice produce no. PDE4D6 phosphodiesterase. Such mice thereby provide means of studying the effects of over-production, or no production, of the PDE4D6 isoforms disclosed according to the invention.

DETAILED SUMMARY OF THE INVENTION

Figure 1:
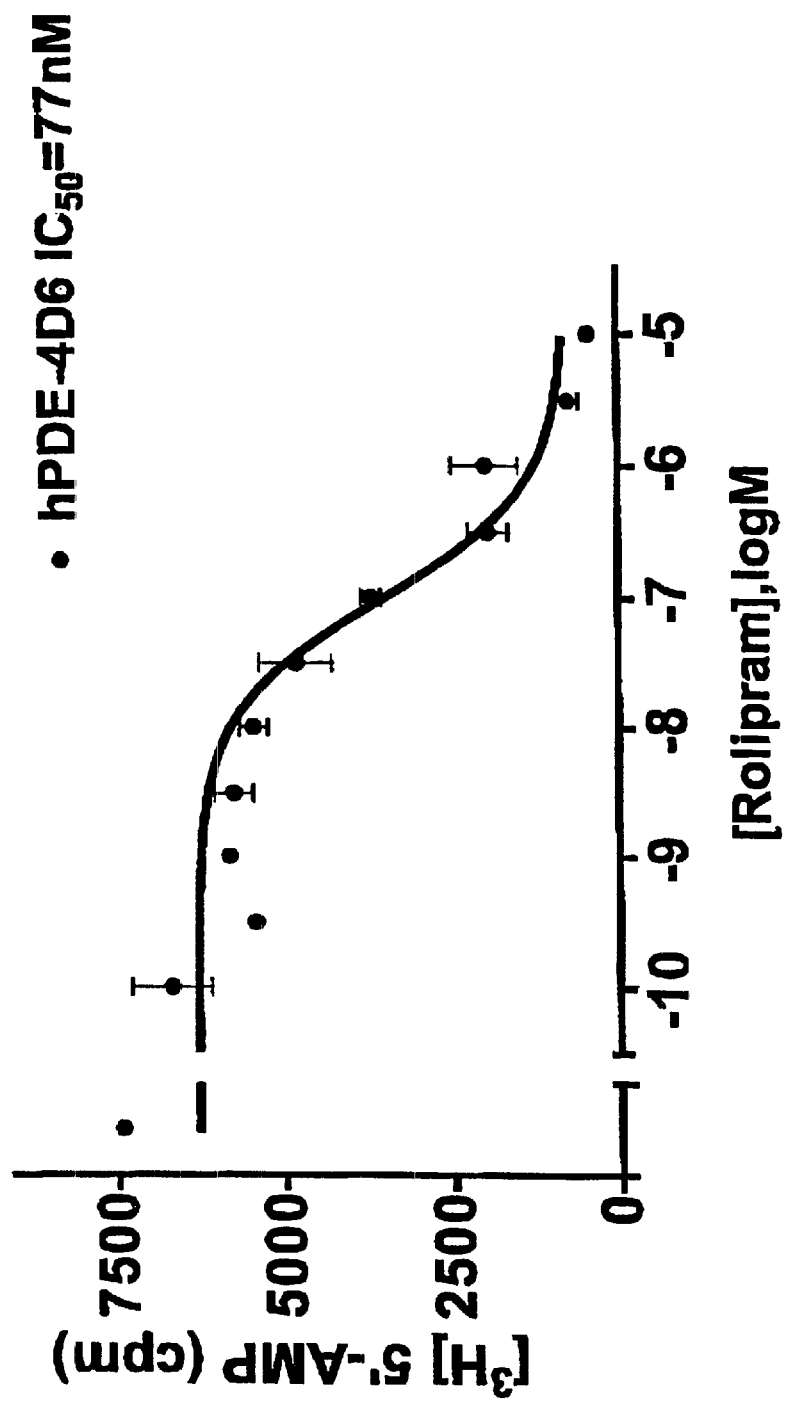
FIG. 1 shows the results of expression of recombinant PDE-4D6 using a baculovirus/SF9 insect expression system. Phosphodiesterase activity was measured in a cell-free system by measuring the decrease in the cAMP hydrolysis product (5'-AMP) after incubation with the recombinant enzyme and in the presence of the indicated concentrations of the phosphodiesterase inhibitor, rolipram. Sensitivity to rolipram is a well-known and distinguishing characteristic of the PDE4 class of phosphodiesterases.

The present invention relates to oligopeptides and polypeptides that contain novel amino acid sequences as shown in SEQ ID NOS: 2 and 4, for the human and rat, respectively), and polynucleotides that encode such polypeptides, e.g., the polynucleotide sequences of SEQ ID NOS: 1 and 3, respectively, as well as segments, fragments, analogs and derivatives of such polypeptides.

The terms "fragment," "derivative" and "analog" when referring to the polypeptide of SEQ ID NOS: 2 or 4 mean a polypeptide which retains essentially the same biological function or activity as such polypeptide, which can include ability to react with an antibody. Thus, an analog includes a proprotein that can be activated by cleavage of the proprotein portion to produce an active mature polypeptide. Such fragments, derivatives and analogs must have sufficient similarity to the polypeptide of SEQ ID NOS: 2 and 4 so that activity of the native polypeptide is retained.

The polypeptide of the present invention may be a recombinant polypeptide, a natural polypeptide or a synthetic polypeptide, preferably a recombinant polypeptide.

The fragment, derivative or. analog of the polypeptide of SEQ ID NO:2 and 4 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence, commonly for the purpose of creating a genetically engineered form of the protein that is susceptible to secretion from a cell, such as a transformed cell. Such fragments, derivatives and analogs are deemed to be within the scope of those skilled in the art from the teachings herein.

The polypeptides of the present invention are preferably provided in an isolated form, and may even be purified to homogeneity, and most commonly will be produced by recombinant expression using any of a large number of such expression systems well known to those of skill in the art.

The term "isolated" means that the material is removed from its original environment (e.g., the natural environment if it is naturally occurring). For example, a naturally occurring polypeptide present in a living animal is not isolated, but the same polypeptide, separated from some or all of the coexisting materials in the natural system, is isolated. Such polypeptides could be part of a composition, and still be isolated in that such composition is not part of its natural environment.

The polypeptides of the present invention include the polypeptide of SEQ ID NO: 2 and 4 (in particular the mature polypeptide) as well as polypeptides which have varying degrees of sequence homology thereto so long as such oligopeptides or polypeptides contain a sequence that is also homologous to the novel 15-mer sequence of SEQ ID NO: 5).

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

More particularly, the polypeptides of the invention include isolated polypeptides, and fragments thereof, comprising an unbroken sequence of at least 15 amino acids (referred to herein as the novel 15-mer (SEQ ID NO: 5), or just as a 15-mer when used generically) having the sequence of the N-terminal 15 amino acids (the N-terminal 15-mer) of the sequences of SEQ ID NOS: 2 and 4) and also given as SEQ ID NO: 5.

In addition to such polypeptides, and fragments thereof, containing the novel 15-mer disclosed according to the invention, there are also disclosed within the present invention polypeptides, and fragments thereof, comprising a 15-mer (i.e., an unbroken sequence of amino acids 15 residues in length) wherein such 15-mer shows sequence homology to the novel 15-mer disclosed herein. Thus, polypeptides, and fragments thereof, within the present invention will contain 15-mer amino acid sequences (i.e., uninterrupted stretches of 15 consecutive amino acids) wherein said 15-mers show at least 65% identity with the novel 15-mer (SEQ ID NO: 5) of the invention, preferably 80% sequence identity thereto, and most preferably 95% sequence identity thereto. Most preferably, such polypeptides, and fragments thereof, will contain the novel 15-mer (SEQ ID NO: 5)(for example, residue 5 of the 15-mer could be Asn or Phe).

In accordance with. the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

The above description for percent identity or percent homology is intended to apply equally to nucleotide or amino acid sequences The polypeptides, and fragments and segments thereof, within the present invention may possess. enzyme activity, commonly phosphodiesterase activity, especially where polypeptides similar in length to those of SEQ ID NOS: 2 and 4, or very large fragments thereof, are involved. Such phosphodiesterases will also include as part of their structure sequences of amino acids possessing sequence homology, or sequence identity, to the novel 15-mer of SEQ ID NO: 5. Thus, phosphodiesterases within the present invention will commonly contain at least one continuous sequence of amino acids having at least 65% sequence identity to the novel 15-mer (SEQ ID NO: 5), preferably 80% sequence identity thereto, and most preferably 95% or 97% sequence identity thereto, with the preferred embodiment of such phosphodiesterase containing the novel 15-mer (SEQ ID NO: 5) within its amino acid sequence.

Polypeptides, and fragments or segments thereof, within the present invention may also contain unbroken stretches of amino acids containing less than the full 15 amino acids of the novel 15-mer (SEQ ID NO: 5) disclosed herein. Thus, polypeptides, and fragments thereof, within the present invention may also contain an unbroken sequence of as few as 10 amino acids (a 10-mer), said 10-mer being identical to an unbroken 10-mer wholly within the novel 15-mer disclosed herein (SEQ ID NO: 5). Preferably, said polypeptides, and fragments thereof, will contain at least a 1 2-mer, or an unbroken sequence of 12 amino acids also found as an unbroken sequence within the novel 15-mer disclosed according to the invention. Further, polypeptides, and fragments thereof, will most preferably contain within their sequences at least one unbroken sequence of 15 amino acids identical to the novel 15-mer (SEQ ID NO: 5) disclosed herein, such 15-mer thereby showing 100% sequence identity to the novel 15-mer of the invention SEQ ID NO: 5).

As used with respect to the polypeptides (and polynucleotides) of the present invention, the term segment refers to a sequence that is a subset of a larger sequence (i.e., a continuous or unbroken sequence of residues within a larger sequence). Thus, for example, the 15 residues of SEQ ID NO: 5 (referred to herein as the novel 15-mer) can contain a total of 6 segments of 10 residues each (e.g. 1–10, 2–11, 3–12, 4–13, 5–14, and 6–15).

Consequently, in terms of the subset of segments within the novel 15-mer of SEQ ID NO: 5, the polypeptides of the present invention include polypeptides comprising a 15 amino acid segment having a sequence at least 65% identical, preferably 80% identical, more preferably 95% identical, and most preferably 100% identical to SEQ ID NO: 5.

Alternatively, the polypeptides of the present invention include polypeptides comprising a segment within SEQ ID NO: 5, said segment containing at least 10 amino acids, preferably 122 amino acids, and more preferably 14 amino acids, and most preferably 15 amino acids (the latter being equal to SEQ ID NO: 5).

In addition, the polypeptides, and fragments thereof, of the present invention may be found in the cells and tissues of any species of animal, but will preferably be found in cells from mammals, especially the cells of humans. In any given animal, the polypeptides, and fragments thereof, within the present invention may be found in a variety of tissues, especially the nervous system, most especially the brain, for example, in the hippocampal region.

The present invention also includes novel polynucleotides, especially novel cDNAs derived from mRNAs found in the cells of animals and which code for the polypeptides of the invention. The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO:1 or 3, or may be a different coding sequence, which coding sequence, as a result of the redundancy or degeneracy of the genetic code, encodes the same mature polypeptide as the DNA of SEQ ID NO: 1 or 3.

The term "polynucleotide" as used for the present invention encompasses a polynucleotide, which includes only coding sequence for the polypeptide, as well as a polynucleotide that includes additional coding and/or non-coding sequence.

The polynucleotides of the present invention (SEQ ID NOS: 1 and 3) contain open reading frames available for the coding of polypeptide amino acid sequences. For the sequence of SEQ ID NO: 1, the open reading frame (or ORF) coding for the polypeptide of SEQ ID NO: 2 (the human hippocampal PDE4D6 isoform) is found at nucleotides 357–1991 (with nucleotides 1912–1914 representing the "taa" terminating codon) while for the rat isoform, the sequence of SEQ ID NO: 3 contains an open reading frame at nucleotides 332–1882 (with nucleotides 1883–1885 representing the "taa". terminating codon).

The present invention further relates to variants of such polynucleotides which encode for fragments, analogs and derivatives of the polypeptide having the amino acid sequence of SEQ ID NO: 2 and 4. Variants of the polynucleotide may be naturally occurring allelic variants of the polynucleotide or a non-naturally occurring variant of the polynucleotide.

Thus, the present invention includes polynucleotides encoding all of the polynucleotides, and fragments thereof, as disclosed hereinabove provided that they incorporate therein a close homolog of the novel 15-mer of SEQ ID NO: 5, such as a 15-mer having at least a 65% sequence identity to the novel 15-mer of SEQ ID NO: 5. The present invention also includes the novel oligonucleotide sequence coding for the novel-15 mer polypeptide (SEQ ID NO: 5) disclosed herein.

Such polynucleotides may have a coding sequence which is a naturally occurring allelic variant of the coding sequence shown in SEQ ID NO: 1 and 3. As known in the art, an-allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell and a transmembrane anchor which facilitates attachment of the polypeptide to a cellular membrane. The polypeptide having a leader sequence is a proprotein and may have the leader sequence cleaved by the host cell to form the mature form of the polypeptide. The polynucleotides may also encode for a proprotein which is the mature protein plus additional N-terminal amino acid residues. A mature protein having a prosequence is a proprotein and is an inactive form of the protein. Once the prosequence is cleaved an active mature protein remains.

Thus, for example, a polynucleotide of the present invention may encode for a mature protein, for a protein having a prosequence, for a protein having a transmembrane anchor or for a polypeptide having a prosequence, a presequence (leader sequence) and a transmembrane anchor.

Polynucleotides of the present invention may also have the coding sequence fused in frame to a marker sequence that allows for purification of the polypeptide of the present invention. The marker sequence may be a hexa-histidine tag (possibly supplied by a pQE-9 vector) to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

As used herein, the term "gene" means the segment of DNA involved in producing a polypeptide chain; it includes regions preceding and following the coding region (leader and trailer) as well as intervening sequences (introns) between individual coding segments (exons). Of course, cDNAs will lack the corresponding introns.

Fragments of the full-length polynucleotide of the present invention may be used as a hybridization probe for a cDNA library to isolate the full-length cDNA and to isolate other cDNAs, which have a high sequence similarity to the gene or similar biological activity. Probes of this type preferably have at least 30 bases and will be homologous to the sequence coding for the novel 15-mer disclosed in SEQ ID NO: 5. Such probes may also have 45 or more bases but will again contain sequences homologous to a sequence coding for the novel 15-mer of SEQ ID NO: 5, or a variant thereof within the invention. Because of the degeneracy of the genetic code, many such sequences will be found to be homologous to sequences coding for the novel 15-mer disclosed herein. The set of such sequences will also include those that code for amino acid sequences that are themselves homologous to the novel 15-mer (SEQ ID NO: 5).

The polynucleotides. of the invention, in particular the polynucleotide coding for the novel 15-mer (SEQ ID NO: 5) disclosed herein, may also serve as a site for study of possible mutation of said sequence, especially where mutations occurring in disease conditions are related to excess amounts of intracellular phosphodiesterase activity. Thus, the polynucleotide sequence coding for the novel 15-mer may act as a reference for the development of probes, possibly as long as 30 to 45 nucleotides, or longer, that can be used to probe the genome of animals suspected of being at risk for disease, or possibly having such disease, especially where such disease may involve altered levels of cAMP within the cells of such animals, such as rats and mice, and especially humans,.and most especially where this occurs within neurons of the brain, most especially those areas of the brain involved in memory, such as long term memory, for example, the hippocampal region. Thus, such stretches of nucleotides will serve as sites for the binding of probes that will identify possible causes of such diseases, especially diseases involving loss of memory, most especially long-term memory.

The present invention also relates to vectors which contain polynucleotides of the present invention, host cells which are genetically engineered with vectors of the invention, especially where such cells result in a cell line that can be used for assay of PDE-4D, especially PDE-4D6, activity and production of polypeptides of the invention by recombinant techniques.

Host cells, preferably insect cells of Spodoptera species, most especially SF9 cells, are genetically engineered (transduced or transformed or transfected) with the vectors, especially baculovirus) of this invention which may be, for example, a cloning vector or an expression vector. Such vectors can include plasmids, viruses and the like. The engineered host cells are cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well. as an appropriate promoter or control sequence, may be employed to transform an appropriate host to permit the host to express the protein. Such transformation will be permanent and thus give rise to a cell line that can be used for further testing. Such cell lines used for testing will commonly be mammalian cells whose cAMP levels are to be monitored for indications of varying phosphodiesterase (PDE4D) activity.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9 (and other insect expression systems); animal cells such as CHO, COS or Bowes melanoma; adenoviruses; plant cells, etc. The selection of an appropriate host is deemed to be within the knowledge of those skilled in the art based on the teachings herein.

More particularly, the present invention also includes recombinant constructs comprising one or more of the sequences as broadly described above. The constructs, comprise a vector, such as a plasmid or viral vector, especially where the Baculovirus/SF9 vector/expression system is used, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can. be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). A preferred embodiment utilizes expression from insect cells, especially SF9 cells from *Spodoptera frugiperda*.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), *Recombinant Gene Expression Protocols, in Methods in Molecular Biology*, Vol. 62, (Tuan, ed., Humana Press, Totowa, N.J., 1997), and *Current Protocols in Molecular Biology*, (Ausabel et al, Eds.,), John Wiley & Sons, NY (1994–1999), the disclosures of which are hereby incorporated by reference in their entirety.

Transcription of the DNA encoding the polypeptides of the present invention by higher eukaryotes is increased by inserting an enhancer sequence into the vector. Enhancers are cis-acting elements. of DNA, usually about from 10 to 300 bp that act on a promoter to increase its. transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* Trp1 gene, and a promoter derived from a highly expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Use of a Baculovirus-based expression system is a preferred and convenient method of forming the recombinants disclosed herein. Baculoviruses represent a large family of DNA viruses that infect mostly insects. The prototype is the nuclear polyhedrosis virus (AcMNPV) from *Autographa californica*, which infects a number of lepidopteran species. One advantage of the baculovirus system is that recombinant baculoviruses can be produced in vivo. Following co-transfection with transfer plasmid, most progeny tend to be wild type and a good deal of the subsequent processing involves screening. To help identify plaques, special systems are available that utilize deletion mutants. By way of non-limiting example, a recombinant AcMNPV derivative (called BacPAK6) has been reported in the literature that includes target sites for the restriction nuclease Bsu36I upstream of the polyhedrin gene (and within ORF 1629) that encodes a capsid gene (essential for virus viability). Bsf36I does not cut elsewhere in the genome and digestion of the BacPAK6 deletes a portion of the ORF1629, thereby rendering the virus non-viable. Thus, with a protocol involving a system like Bsu361-cut BacPAK6 DNA most of the progeny are non-viable so that the only progeny obtained after co-transfection of transfer plasmid and digested BacPAK6 is the recombinant because the transfer plasmid, containing the exogenous DNA, is inserted at the Bsu36I site thereby rendering the recombinants resistant to the enzyme. [see Kitts and Possee, A method for producing baculovirus expression vectors at high frequency, *BioTechniques*, 14, 810–817 (1993). For general procedures, see King and Possee, *The Baculovirus Expression System: A Laboratory Guide*, Chapman and Hall, New York (1992) and *Recombinant Gene Expression Protocols*, in *Methods in Molecular Biology*, Vol. 62, (Tuan, ed., Humana Press, Totowa, N.J., 1997), at Chapter 19, pp. 235–246.

Figure 2:
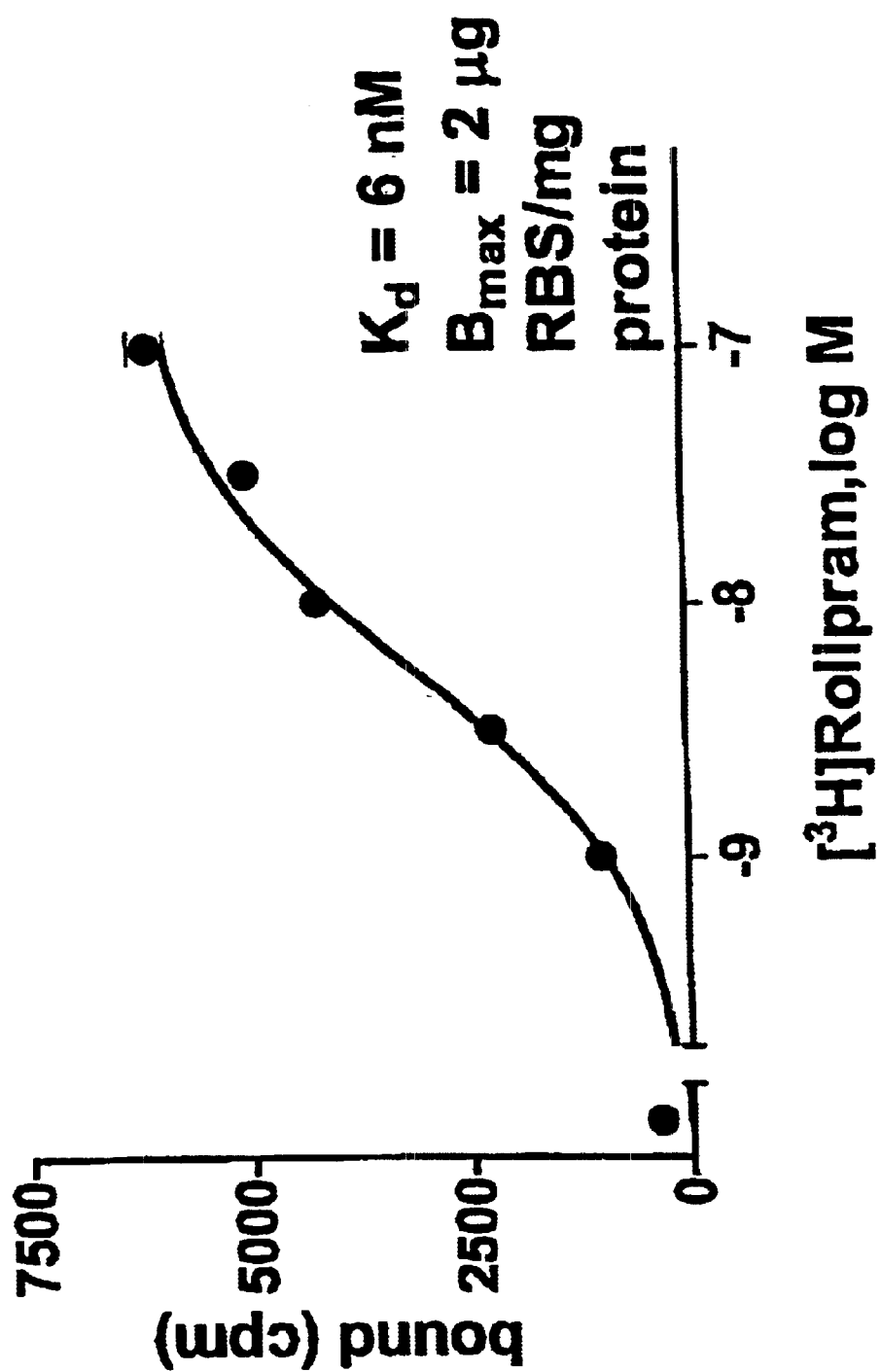
FIG. 2 shows binding of $^3$H-rolipram to the expressed recombinant PDE-4D6. The indicated concentrations of labeled rolipram were incubated with insect lysates containing recombinant PDE-4D6 and binding of rolipram was measured after rapid filtration on glass fiber filters. Here, RBS stands for rolipram binding sites; $K_d$ refers to the dissociation constant.
Figure 3:
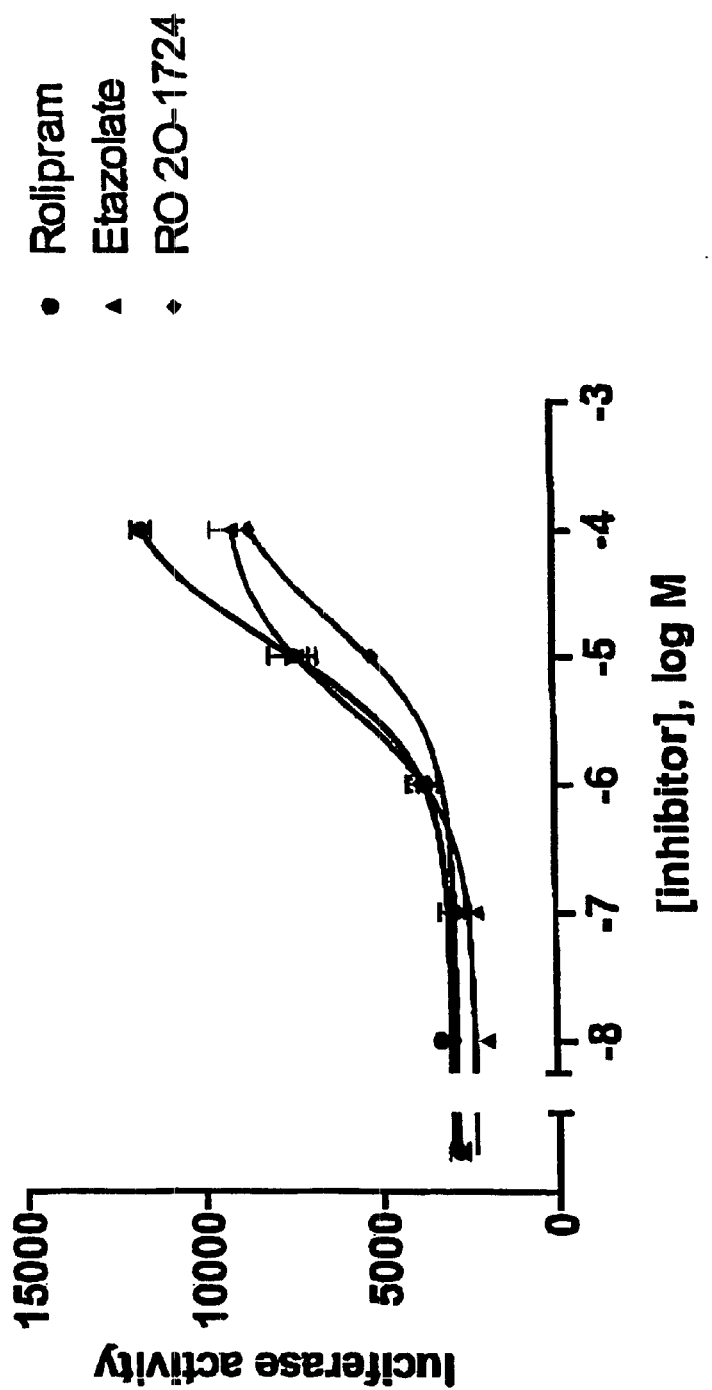
FIG. 3 shows that expression of recombinant PDE-4D6 in mammalian cells reduces cAMP levels. Here, Chinese hamster ovary (CHO) cells were transfected with PDE-4D6 and a CRE-luciferase reporter system that responds to cAMP levels. Basal cAMP levels are reduced and incubation with PDE-4 inhibitors causes an increase in cAMP accumulation as detected by an increase in the activity of the CRE-luciferase reporter gene.

The effect of known inhibitors, such as rolipram, on the PDE-4D6 of the present invention (using recombinant PDE-4D6 of the present invention expressed in a Baculovirus/SF9 insect cell expression system) is shown in FIG. 1. Rolipram is a well known inhibitor of such enzymes (see, for example, Livi et al, "Cloning and Expression of cDNA for a human low $_{KM}$ rolipram sensitive cyclic AMP phosphodiesterase," *Molecular and Cellular Biol.*, 10, 2678–2686 (1990))Thus, the PDE-4D6 of the present invention is sensitive to rolipram as are other PDE4 enzymes. Binding of rolipram to the PDE-4D6 of the present invention is shown in FIG. 2. The results of the experiments depicted in FIG. 3 show clearly the expression of the PDE-4D6 of the present invention in mammalian cells distinctly reduces the levels of cAMP in those cells.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO cells (as utilized in the methods disclosed herein), HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The invention disclosed herein also relates to a transgenic animal comprising within its genome one or more copies of the polynucleotides encoding the novel polypeptides of the invention. The transgenic animals of the invention may contain within their genome multiple copies of the polypeptides encoding the polypeptides of the invention, or one copy of a gene encoding such polypeptide but wherein said gene is linked to a promoter that will direct overexpression of said polypeptide within some, or all, of the cells of said transgenic animal. The transgenic animal of the invention will preferably be a mammal, most preferably a mouse.

The present invention also relates to a transgenic animal whose genome lacks a gene expressing a functional PDE4D6 isoform or functional analog thereof, such animal commonly being referred to as a "knockout" animal, especially a "knock-out mouse."

The present invention also relates to a transgenic non-human animal whose genome comprises one or more genes coding for the human isoform of PDE4D6 disclosed herein. in place of the mammalian gene otherwise coding for said the non-human isoform. Most preferably said animal will be a mouse.

Such methods of producing transgenic animals are well within the skill of those in the art and will not be described in detail herein. [See: Wu et al, *Methods in Gene Biotechnology*, CRC 1997, pp.339–366; Jacenko, O., *Strategies in Generating Transgenic Animals*, in *Recombinant Gene Expression Protocols*, Vol. 62 of *Methods in Molecular Biology*, Humana Press, 1997, pp 399–424]

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps. [See: Salanova et al, Heterologous Expression and Purification of Recombinant Rolipram-Sensitive Cyclic AMP-Specific Phosphodiesterases, in *Methods: A Companion to Methods in Enzymology* 14:55–64 (1998)]

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The full-length polypeptides of the present invention were readily cloned from insect cells using the baculovirus expression vector. Such expression was readily performed using methods well known in the art. [See: Wang et al, Expression, Purification, and Characterization of Human cAMP-Specific Phosphodiesterase (PDE4) Subtypes A, B, C, and D, *Biochem. Biophys. Res. Comm.* 234, 320–324 (1997), in particular, SF9 cells as in Wang et al. The recombinant SPD4D6 enzyme is then available for in vitro assay.

This invention also provides a method of screening compounds to identify those that block (antagonists) interaction of cAMP with PDE4Ds of the invention disclosed herein (designated PDE4D6). Such reaction results in an increased cyclic AMP level within the subject cells and resultant physiological alterations resulting therefrom.

In applying the methods of the invention, it should be kept in mind that the PDE4D6 isoforms disclosed herein are not merely general phosphodiesterases but are particular isoforms involved in the physiological reactions to be monitored. Thus, a given cell will commonly possess a set of isoforms and the goal of the methods and disclosure of the invention are to monitor the levels of the isoforms of the invention (the PDE4D6 isoforms disclosed herein) in neural cells as a means of correlating such enzyme levels with memory. The isoforms of the invention are therefore highly selected isoforms derived from cells in areas of the brain known to be related to memory.

The present invention also relates to an assay for identifying potential antagonists specific for PDE4Ds, in particular, PDE4D6 isoforms. An example of such an assay combines a PDE4D of the invention (i.e., a PDE4d6 isoform) and a potential antagonist (i.e., an inhibitor) under appropriate conditions for a competitive inhibition assay. Other inhibitory substances may even enter cells and bind directly to the DNA neighboring the sequences coding for the polypeptides of the invention, thereby decreasing their expression and thus increasing intracellular levels of cAMP.

Potential antagonists include small chemical compounds or, in some cases, an antibody that binds specifically to the polypeptide of the invention. Such antibodies are useful as a means of detecting the polypeptides, and fragments thereof, of the present invention.

Another potential antagonist or inhibitor of the invention is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of PDE4D isoforms. The antisense RNA oligonucleotide hybridizes to the mRNA in vivo and blocks translation. of the mRNA molecule into a PDE4D polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of PDE4Ds, especially PDE4D6.

Potential modulators, either inhibitors or even activators, include small molecules that bind to and occupy the catalytic site of the polypeptide thereby making the catalytic site inaccessible to substrate such that normal biological activity is prevented. Examples of small molecules include but are not limited to small chemical compounds, especially those having cyclic nucleotide-like structures. Other potential modulators are peptides, and peptide analogs. Such modulators, either inhibitors or activators, can be assayed in vivo using both the knock-out mice already described, as well as the humanized mice in which a human gene coding for the human isoform of PDE4D6 disclosed herein is present in place of the mouse gene otherwise coding for such analog.

This invention is also related to the use of the genes coding for the polypeptides of the invention as a diagnostic tool. Detection of a mutated form of the gene will allow a diagnosis of a disease or a susceptibility to a disease that results from expression of a mutated PDE4D polypeptide that may have, for example, increased activity in degrading cAMP.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the novel 15-mer of SPD4D6 can be used to identify and, analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by. the direct DNA sequencing method. In addition, cloned DNA. segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high-resolution gel electrophoresis. DNA fragments of different sequences may be distinguished on denaturing formamide gradient gels in which the mobilities of. different DNA.fragments are retarded in the gel at different positions according to their specific melting or partial melting temperatures (see, e.g., Myers et al., Science, 230:1242 (1985)).

The methods of the invention thus. provide for a process for diagnosing a disease in an animal afflicted therewith, or a susceptibility to a disease in an animal at risk thereof, comprising determining a mutation in the genome of a neuron from said animal and wherein the mutation occurs in a nucleotide sequence coding for the 15-mer of SEQ ID NO:5. Such animal is preferably a mammal and most preferably a human, wherein the disease to be determined is one involving. loss of memory as a primary or secondary condition, especially loss of long term memory.

In addition, sequence changes at specific locations may also be revealed by nuclease protection assays, such as RNase and S1 protection or the chemical cleavage method (e.g., Cotton et al., PNAS, USA, 85:4397–4401 (1985)) and these are deemed within the methods of the invention.

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The polynucleotides coding for the novel 15-mer of the invention, and homologs thereof, are specifically targeted to and can hybridize with a particular location on an individual human chromosome. Moreover, there is a current need for identifying particular sites on the chromosome, for example, as part of the human genome project. Thus, sequences can be mapped to chromosomes by preparing PCR primers (preferably 15–25 bp) from the cDNA.

Fluorescence in situ hybridization (FISH) of a cDNA clone to a metaphase chromosomal spread can likewise be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988). The chromosomal location of PDE genes (including PDE4D) is known to those skilled in the art.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a non-human. The antibody so obtained will then bind the polypeptide itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Such antibodies find use in assays to detect the presence of aberrant forms of the polypeptides disclosed herein, especially where the sequences differ from that found in the novel 15-mer (SEQ ID NO: 5) disclosed according to the invention, which sequence may be unique to PDE4D enzymes found in cells of the hippocampal region (a region known to be involved in memory).

As already described, in the brain the level of cAMP within neurons is believed to be related to the quality of memory, especially long-term memory. Thus, since PDE4D degrades cAMP, the level of this enzyme could have effects on memory in animals, for example, in humans. Briefly, a compound that inhibits cAMP phosphodiesterase (PDE) will thereby increase intracellular levels of cAMP, which in turn activate a protein kinase that phosphorylates a transcription factor (cAMP response binding protein), which transcription factor then binds to a DNA promoter sequence to activate genes that are important in long term memory. The more active such genes are, the better is long term memory. Thus, by inhibiting the phosphodiesterase, long term memory can be enhanced.

The present invention also provides for a means of examining actual or potential disease conditions involving altered levels of cAMP by determining the presence or absence of novel polypeptides of the invention in an animal suspected of having such a disease condition or being at risk therefor. Thus, the methods of the invention provide a process for diagnosing a disease in an animal afflicted therewith, or diagnosing a susceptibility to a disease in an animal at risk thereof, wherein said disease is related, for example, to an over-expression of a phosphodiesterase according to the invention (i.e., one incorporating in its structure a sequence homologous to the novel 15-mer of SEQ ID NO: 5 comprising determining the level of said phosphodiesterase activity in a cell from said animal, wherein said animal is preferably a mammal and most preferably a human. The disease conditions to be so determined will often involve loss of memory as a primary or secondary effect thereof, especially loss of long term memory, and the cells to be tested will commonly be neurons, especially those of the brain, for example, neurons of the hippocampal region.

The methods of the present invention are also directed to facilitating the development of potentially useful therapeutic agents that may be effective in combating loss of memory, especially long term memory, or which may be effective in restoring memory, especially long term memory, or which may play a role in causing the loss of memory, especially long term memory, perhaps by activating brain, especially hippocampal, neuronal cAMP phosphodiesterase, particularly the PDE4D6 activity disclosed herein and thereby decreasing levels of cAMP in such cells.

In keeping with this objective, the present invention provides a means of screening small compounds for the ability to inhibit PDE4D isoforms, especially those disclosed herein. Such screening is conveniently done either in vitro in whole cells in culture by first preparing cells into which have been inserted the appropriate DNAs to form a cell line expressing the polypeptides of the present invention.

Using the methods disclosed herein the polynucleotides coding for the novel phosphodiesterases of the invention can be inserted into an appropriate vector and said vector transfected into an appropriate host cell, such as CHO cells, to create a stable cell line. The cAMP levels of such cells, and thereby the level of PDE4D phosphodiesterase activity in such cells, can be used to monitor the effects of various chemical agents on phosphodiesterase activity.

More specifically, CHO cells, stably expressing phosphodiesterase, such as the PDE4D isoforms of the present invention, can be readily utilized for assays of cAMP. [See: Pon et al, Characterization of CHO-K1 Cells Stably Expressing PDE-IV Enzymes, *Cell Biochemistry and Biophysics* 29:159–178 (1998) the disclosure of which is incorporated herein] Such cells have been shown to readily express recombinant full-length cAMP phosphodiesterases.

Measurements of whole cell cyclic AMP in response to the presence of potential PDE inhibitory substances in the medium have been described. [See Pon et al (1998)] Briefly, CHO cells expressing the PDE isoform are lysed by sonication for 10 seconds in ice-cold solution containing Tris pH 7.5 buffer (50 mM Tris, 1 mM EDTA) and protease inhibitor added along with 200 $\mu$M $\beta$-mercaptoethanol. Centrifugation at 100,000 g for 90 minutes at 4° C. yields soluble and particulate fractions containing phosphodiesterase activity. The phosphodiesterase activity is then measured in a solution containing 50 mM Tris (pH 7.5), 10 mM $MgCl_2$, 1 mM EDTA and 100 nM $^3$H-cAMP (with final volume of 100 $\mu$L) and containing varying concentrations of inhibitors to be screened. After incubation at 30° C. for periods up to 10 minutes, the reaction was terminated by addition of about 50 $\mu$L PDE scintillation proximity assay (SPA) beads (from Amersham) containing 18 mM $ZnSO_4$. Scintillation counting then gave the amount of hydrolysis of $^3$H-cAMP. This represents an in vitro assay for cAMP.

In the same way, the cells can also be grown in a culture medium containing potential inhibitory agents of phosphodiesterase isoforms and the cellular cAMP measured in a similar fashion after the cells are removed from the inhibitory medium. This may be necessary because Pon et al have found that cAMP phosphodiesterases demonstrate differences in activity when assayed in whole cell as opposed to lysed cells.

The overall screening process for phosphodiesterase inhibitory activity would be one comprising: contacting a cell expressing a polypeptide coded for by a polynucleotide of the invention with a chemical agent having potential phosphodiesterase moderating, either activating or inhibiting, activity and measuring the level of total cyclic adenosine monophosphate (cAMP) in said cell following said exposure wherein an altered level of cAMP in said cell following said exposure is an indicator of such moderating activity.

More specifically, an increase in cAMP level indicates an inhibitory activity by the agent being tested while a decrease in cAMP level indicates an activating effect by the agent being tested.

Thus, using the novel polypeptides of the invention disclosed herein, together with the methods disclosed herein, it is a straightforward procedure to screen potential agents for their ability to alleviate the effects of, or possibly prevent entirely, the effects of memory loss, especially the effects of long term memory loss.

EXAMPLE 1

Isolation of Rat and Human PDE4D6 cDNA Using 5'-RACE Technique

Three nested reverse primers were designed based on the rat PDE4D2 sequence from Genbank (Accession No. u09456) and on the human PDE4D sequence from Genbank (Accession No. u79571). Here, the primer sequences were:

For rat:
RatPDE4DR1: 5'-ATGCAGAGGCCGGTTGCC AGACAGCTCCGCTATTCGG-3' SEQ ID NO: 6
RatPDE4DR2: 5'-TGGCCAGGACATCTTCC TGCTCTGTTTTAACC-3' SEQ ID NO: 7
RatPDE4DR3: 5'-GTCAGGCTGGAGCTGTGCA TCAACTTCTTGACC-3' SEQ ID NO: 8
Human primer sequences are:
HuPDE4DR1: 5'-CCGGTTACCAGACAACTCTGC-3' SEQ ID NO: 9
HuPDE4DR2: 5'-TGGCAAGGACATCTTCTTGTTCA-3' SEQ ID NO: 10
HuPDE4DR3: 5'-GACTCCACTGATCTGAGACATTGGTCT-3' SEQ ID NO: 11

The polymerase chain reaction was performed using a 5' RACE kit (GIBCO-BRL). for searching novel PDE4D cDNA isoforms in 5' ends from rat and human brain tissues. Total RNA from rat hippocampal CA1 region and mRNA from human hippocampus (Clontech) were used-as templates. 1 $\mu$g of RNA samples was used for reverse transcription. The primers used for the first strand cDNA synthesis were ratPDE4DR1 (SEQ ID NO: 6) and huPDE4DR1 (SEQ ID NO: 9). The reverse transcription reaction was carried out with Superscript II RT (GIBCO-BRL) at 42° C. for 1 hour. The cDNA was purified and tailed with poly (C) according to the standard protocol from the 5' RACE kit. The poly (C) tailed cDNA samples were used for PCR with Taq DNA polymerase (GIBCO-BRL). The primers for the PCR reaction were the forward anchor primer (GIBCO-BRL) and rat or human reverse primers (RatPDE4DR2 (SEQ ID NO: 7) or HuPDE4DR2 (SEQ ID NO: 10). The product from the PCR reaction was diluted 1000× and subjected to a second round of PCR with forward primer UAP (GIBCO-BRL) and ratPDE4DR3 (SEQ ID NO: 8) or huPDE4DR3 (SEQ ID NO: 11) nested reverse primers. The PCR products were subcloned using the TA cloning system (Invitrogen) and sequenced. We have also used the rat total brain Marathonma cDNA (Clontech) as template for the 5' RACE and isolated the identical novel PDE4D isoforms.

Full Length Cloning of Rat and Human PDE4D6

Reverse transcription and PCR (RT-PCR) were used to isolate the cDNA encoding the full-length of novel rat and human PDE4D6. Rat hippocampal CA1 and human hippocampal RNA was used as templates. The primers used for the reverse transcription were:

Rat reverse primer 5'AGGTGTGACAGCCTTTACACT-GTTACGT3' SEQ ID NO: 12
Human reverse primer 5'GCACTGTTACGTGTCAG-GAGAA3' SEQ ID NO: 13

The PCR reaction was performed using Pfu DNA polymerase (Stratgene) for 30 cycles using the following primers:

Rat forward primer: RatPDE4DFS (SEQ ID NO: 14)
5'-GACACATAATCTATCAAAAATGCCTGAAGC-3'

Rat reverse primer: RatPDE4DFA (SEQ ID NO: 15)
5'GACAGCCTTTACACTGTTACGTGTCAGG3'

Human forward primer: HuPDE4DFS (SEQ ID NO: 16)
5'-TACATATAATCAATCAAAAATG CCTGAAG CAA-3'

Human reverse primer: HuPDE4DFA (SEQ ID NO: 17)
5'TGTTACGTGTCAGGAGAACGATCA3'.

The PCR products were subcloned into the pCR-Blunt II vector (Invitrogen) and sequenced.

Northern Blot Analysis

Rat and human multiple tissue mRNA blots (Clontech) were prehybridized at 68° C. in buffer containing 6×SSC, 5×Denhardt's solution (0.5% SDS, 0.2% denatured salmon sperm DNA, and 50% formamide) for 2 hours. The N-terminal 200 base pairs of rat and human PDE4D6 cDNA clones were amplified by PCR and used for probes. This region of the cDNA clone represents the novel sequence of PDE4D6. The sequences of rat forward and reverse primers are:

5'-TGGAAAGACGGCTGGATGGG-3' (SEQ ID NO: 18)

5'-TGTAGCCCCAAGACACTGACAA-3' (SEQ ID NO: 19) respectively.

The sequences of human forward and reverse primers are:

5'-TGGGAAGACGGCTGGATGGG-3'(SEQ ID NO: 20)

5'-ATGTAGCCCCAAGACACTGACAGT-3', (SEQ ID NO: 21) respectively.

The PCR products were subcloned into TA cloning vector (Invitrogen). Plasmid DNA was linearized with EcoRV and transcribed with SP6 RNA polymerase and $^{32}$P-UTP using standard procedure. Approximately $10^7$ cpm of the $^{32}$P-labeled riboprobe was hybridized with the Northern blot in 10 ml of the prehybridyzation buffer at 68° C. overnight. After hybridization, the blot was washed three times, 20 minutes each time, with 1×ssc buffer at 68° C. and then exposed to X-ray film (Kodak).

Antiserum Production

Antisera against the novel 15-mer of the invention (for both rat and human isoforms) can be readily generated. Antisera against a conserved catalytic domain of the PDE4D family can also be generated. The peptides were synthesized, conjugated with KLH protein, and used for production of rabbit polyclonal antiserum (Research Genetics Inc.).

EXAMPLE 2

Expression of Rat and Human PDE4D6

The PCR products from Example 1 were then inserted by ligation into a Baculovirus expression system (pBlueBacHis2 from Invitrogen, San Diego, Calif.) in the same way as described above using standard molecular biology procedures.

SF9 cells are then co-transfected with the expression vectors (including the linear AcMNPV DNA (also from Invitrogen). Subsequent steps of cell culturing, recombinant virus purification and titration of viruses are performed by standard methods. [See: O'Reilly, D. R. (1997), Use of Baculovirus Expression Protocols, in *Methods in Molecular Biology*, Vol. 62, Humana Press, NJ). Cells are then grown to a density of about 2 million cells per ml before infecting with recombinant virus at an MOI of about 5. The cells are then cultured for at least 3 days.

The culture media are then pooled and centrifuged to give a pellet that is washed once with PBS and subsequently resuspended in lysis buffer (50 mM Tris-HCl, pH 8.5, 10 mM 2-mercaptoethanol, 1 mM PMSF (phenylmethylsulfonyl chloride) and 1% NP-40) at about 1 ml per 10 million cells, total of about a billion cells. The cells are then sonicated and the homogenate centrifuged for 20 minutes at $.10^4$ g, whereupon the supernatant (containing at least 2 mg of PDE4D6 protein) is collected and mixed at a ratio of 5:2 (v/v) with NiNTA resin (Qiagen, Chatsworth, CA) (the resin already equilibrated with equilibration buffer consisting of 20 mM Tris-HCl, pH 8.0, 500 mM KCl, 20 mM imidazole, 10 mM 2-mercaptoethanol, 10% (v/v) glycerol. The mix is incubated at 4° C. for 30 min with rotation, the resin is packed into a column).

The column is washed with the equilibration buffer until absorption at 280 nm for the eluate is <0.01, then with 2 volumes of wash buffer (20 mM Tris-HCl, pH 8.0, 1 M KCl, 10 mM imidazole, 10 mM 2-mercaptoethanol, 10% (v/v) glycerol) until absorbance of the eluate at 280 nm is <0.01. The recombinant PDE4D6 is then eluted (at a flow rate of about 1 ml/min) with eluting buffer (20 mM Tris-HCl,. pH 8.5, 100 mM KCl, 100 mM imidazole, 10 mM 2-mercaptoethanol, 10% (v/v) glycerol.

The fractions (1 ml each) are collected for subsequent analysis. The fractions are assayed for protein using the BioRad procedure with human serum albumin as standard. In addition, SDS-polyacrylamide gel electrophoresis was run on the fractions. The fractions are also assayed using Western blotting and antibodies already available for PDE4D proteins using C-terminal oligopeptides (see Wang et al, 1997) (conjugated to KLH for immunization in rabbits). Enzyme activity is assayed by standard procedures [Amersham's PDE[$^3$H]cAMP SPA (Scintillation Proximity Assay) Enzyme Assay kit. Here, the enzyme activity is measured in a reaction mixture containing 50 mM Tris, pH 7.5, 10 mM MgCl$_2$, 1 mM EDTA, and appropriate concentration of [$^3$H]cAMP (as indicated in the kit) to final volume of 100 µL (with varying samples of enzyme solution (i.e., column fractions). The reaction mixture containing enzyme is then incubated for 10 minutes at 30° C. in 96-well plates. The reaction is terminated by the addition of 50 µL of the SPA beads (containing 18 mM ZnSO$_4$). The amount of [$^3$H]cAMP hydrolyzed is measured using a scintillation counter.

This assay is also employed for screening potential modulators of the disclosed cAMP phosphodiesterase by including in the reaction mixture the appropriate dilutions of a potential modulator to be screened. Of course, such modulator can be either an inhibitor or an activator of the phosphodiesterase.

What is claimed is:

1. An isolated polypeptide comprising an amino acid sequence that is at least 90% identical to SEQ ID NO: 2, provided said polypeptide comprises an amino acid sequence that is at least 90% identical to SEQ ID NO: 5 and wherein said polypeptide has phosphodiesterase activity.

2. The isolated polypeptide of claim 1, which comprises an amino acid sequence that is at least 95% identical to SEQ ID NO: 5.

3. The isolated polypeptide of claim 1, which comprises SEQ ID NO: 5.

4. An isolated polypeptide comprising an amino acid sequence that is at least 90% identical to SEQ ID NO: 4, provided said polypeptide comprises an amino acid sequence that is at least 90% identical to SEQ ID NO: 5 and wherein said polypeptide has phosphodiesterase activity.

5. The isolated pblypeptide of claim 4, which comprises an amino acid sequence that is at least 95% identical to SEQ ID NO: 5.

6. The isolated polypeptide of claim 4, which comprises SEQ ID NO: 5.

7. An isolated polypeptide comprising an amino acid sequence having SEQ ID NO:2.

8. An isolated polypeptide comprising an amino acid sequence having SEQ ID NO:4.

9. An isolated 15-mer peptide containing at least 12 contiguous amino acids residues of SEQ ID NO: 5 and wherein said 15-mer can elicit in a mammal an antibody production specific for SEQ ID NO: 5.

10. The isolated 15-mer of claim 9, wherein the segment contains at least 14 contiguous amino acid residues of SEQ ID NO: 5.

* * * * *

SEQUENCE LISTING

<160> NUMBER OF SEQ ID NOS: 21

<210> SEQ ID NO 1
<211> LENGTH: 1917
<212> TYPE: DNA
<213> ORGANISM: Artificial Sequence
<220> FEATURE:
<223> OTHER INFORMATION: Description of Artificial Sequence:cDNA derived from mRNA of cells of human brain hippocampal region

<400> SEQUENCE: 1

| | | | | | | |
|---|---|---|---|---|---|---|
| cttgcaacta | agcatcttga | catacattat | tcattaagcc | ctggagctcg | ggagagaaag | 60 |
| atgcagaccc | ttagatcttt | agatattcct | ttatcacgtg | gattttcttt | attcagaata | 120 |
| gttgctgaat | tttgtgccat | tctggagtct | tacaaatggc | atgtattcga | tgggaagacg | 180 |
| gctggatggg | atttaatgcg | aggctttctt | atgtatactt | aattaccaaa | aatctttaaa | 240 |
| aactcatact | ctgcgtggct | tgtggaggtt | gttaaagtgt | cgagattttg | aagctaaata | 300 |
| catttagagc | ttactatata | tatacatata | tatatatata | catataatca | atcaaaaatg | 360 |
| cctgaagcaa | actatttact | gtcagtgtct | tggggctaca | taaagtttaa | aaggatgctt | 420 |
| aatcgggagc | tcacccatct | ctctgaaatg | agtcggtctg | gaaatcaagt | gtcagagttt | 480 |
| atatcaaaca | cattcttaga | taagcaacat | gaagtggaaa | ttccttctcc | aactcagaag | 540 |
| gaaaaggaga | aaagaaaag | accaatgtct | cagatcagtg | gagtcaagaa | attgatgcac | 600 |
| agctctagtc | tgactaattc | aagtatccca | aggtttggag | ttaaaactga | acaagaagat | 660 |
| gtccttgcca | aggaactaga | agatgtgaac | aaatggggtc | ttcatgtttt | cagaatagca | 720 |
| gagttgtctg | gtaaccggcc | cttgactgtt | atcatgcaca | ccatttttca | ggaacgggat | 780 |
| ttattaaaaa | catttaaaat | tccagtagat | actttaatta | catatcttat | gactctcgaa | 840 |
| gaccattacc | atgctgatgt | ggcctatcac | aacaatatcc | atgctgcaga | tgttgtccag | 900 |
| tctactcatg | tgctattatc | tacacctgct | ttggaggctg | tgtttacaga | tttggagatt | 960 |
| cttgcagcaa | tttttgccag | tgcaatacat | gatgtagatc | atcctggtgt | gtccaatcaa | 1020 |
| tttctgatca | atacaaactc | tgaacttgcc | ttgatgtaca | atgattcctc | agtcttagag | 1080 |
| aaccatcatt | tggctgtggg | ctttaaattg | cttcaggaag | aaaactgtga | cattttccag | 1140 |
| aatttgacca | aaaacaaag | acaatcttta | aggaaaatgg | tcattgacat | cgtacttgca | 1200 |
| acagatatgt | caaaacacat | gaatctactg | gctgatttga | agactatggt | tgaaactaag | 1260 |
| aaagtgacaa | gctctggagt | tcttcttctt | gataattatt | ccgataggat | tcaggttctt | 1320 |
| cagaatatgg | tgcactgtgc | agatctgagc | aacccaacaa | agcctctcca | gctgtaccgc | 1380 |
| cagtggacgg | accggataat | ggaggagttc | ttccgccaag | gagaccgaga | gagggaacgt | 1440 |
| ggcatggaga | taagccccat | gtgtgacaag | cacaatgctt | ccgtggaaaa | atcacaggtg | 1500 |
| ggcttcatag | actatattgt | tcatcccctc | tgggagacat | gggcagacct | cgtccaccct | 1560 |
| gacgcccagg | atattttgga | cactttggag | gacaatcgtg | aatggtacca | gagcacaatc | 1620 |
| cctcagagcc | cctctcctgc | acctgatgac | ccagaggagg | gccggcaggg | tcaaactgag | 1680 |
| aaattccagt | ttgaactaac | tttagaggaa | gatggtgagt | cagacacgga | aaaggacagt | 1740 |
| ggcagtcaag | tggaagaaga | cactagctgc | agtgactcca | agactctttg | tactcaagac | 1800 |
| tcagagtcta | ctgaaattcc | ccttgatgaa | caggttgaag | aggaggcagt | agggaagaa | 1860 |
| gaggaaagcc | agcctgaagc | ctgtgtcata | gatgatcgtt | ctcctgacac | gtaacag | 1917 |

```
<210> SEQ ID NO 2
<211> LENGTH: 518
<212> TYPE: PRT
<213> ORGANISM: Homo sapiens

<400> SEQUENCE: 2

Met Pro Glu Ala Asn Tyr Leu Leu Ser Val Ser Trp Gly Tyr Ile Lys
 1               5                  10                  15

Phe Lys Arg Met Leu Asn Arg Glu Leu Thr His Leu Ser Glu Met Ser
                20                  25                  30

Arg Ser Gly Asn Gln Val Ser Glu Phe Ile Ser Asn Thr Phe Leu Asp
            35                  40                  45

Lys Gln His Glu Val Glu Ile Pro Ser Pro Thr Gln Lys Glu Lys Glu
        50                  55                  60

Lys Lys Lys Arg Pro Met Ser Gln Ile Ser Gly Val Lys Lys Leu Met
 65                  70                  75                  80

His Ser Ser Ser Leu Thr Asn Ser Ser Ile Pro Arg Phe Gly Val Lys
                85                  90                  95

Thr Glu Gln Glu Asp Val Leu Ala Lys Glu Leu Glu Asp Val Asn Lys
            100                 105                 110

Trp Gly Leu His Val Phe Arg Ile Ala Glu Leu Ser Gly Asn Arg Pro
        115                 120                 125

Leu Thr Val Ile Met His Thr Ile Phe Gln Glu Arg Asp Leu Leu Lys
    130                 135                 140

Thr Phe Lys Ile Pro Val Asp Thr Leu Ile Thr Tyr Leu Met Thr Leu
145                 150                 155                 160

Glu Asp His Tyr His Ala Asp Val Ala Tyr His Asn Asn Ile His Ala
                165                 170                 175

Ala Asp Val Val Gln Ser Thr His Val Leu Leu Ser Thr Pro Ala Leu
            180                 185                 190

Glu Ala Val Phe Thr Asp Leu Glu Ile Leu Ala Ala Ile Phe Ala Ser
        195                 200                 205

Ala Ile His Asp Val Asp His Pro Gly Val Ser Asn Gln Phe Leu Ile
    210                 215                 220

Asn Thr Asn Ser Glu Leu Ala Leu Met Tyr Asn Asp Ser Ser Val Leu
225                 230                 235                 240

Glu Asn His His Leu Ala Val Gly Phe Lys Leu Leu Gln Glu Glu Asn
                245                 250                 255

Cys Asp Ile Phe Gln Asn Leu Thr Lys Lys Gln Arg Gln Ser Leu Arg
            260                 265                 270

Lys Met Val Ile Asp Ile Val Leu Ala Thr Asp Met Ser Lys His Met
        275                 280                 285

Asn Leu Leu Ala Asp Leu Lys Thr Met Val Glu Thr Lys Lys Val Thr
    290                 295                 300

Ser Ser Gly Val Leu Leu Leu Asp Asn Tyr Ser Asp Arg Ile Gln Val
305                 310                 315                 320

Leu Gln Asn Met Val His Cys Ala Asp Leu Ser Asn Pro Thr Lys Pro
                325                 330                 335

Leu Gln Leu Tyr Arg Gln Trp Thr Asp Arg Ile Met Glu Glu Phe Phe
            340                 345                 350

Arg Gln Gly Asp Arg Glu Arg Glu Arg Gly Met Glu Ile Ser Pro Met
        355                 360                 365

Cys Asp Lys His Asn Ala Ser Val Glu Lys Ser Gln Val Gly Phe Ile
    370                 375                 380
```

```
Asp Tyr Ile Val His Pro Leu Trp Glu Thr Trp Ala Asp Leu Val His
385                 390                 395                 400

Pro Asp Ala Gln Asp Ile Leu Asp Thr Leu Glu Asp Asn Arg Glu Trp
            405                 410                 415

Tyr Gln Ser Thr Ile Pro Gln Ser Pro Ser Pro Ala Pro Asp Asp Pro
            420                 425                 430

Glu Glu Gly Arg Gln Gly Gln Thr Glu Lys Phe Gln Phe Glu Leu Thr
            435                 440                 445

Leu Glu Glu Asp Gly Glu Ser Asp Thr Glu Lys Asp Ser Gly Ser Gln
            450                 455                 460

Val Glu Glu Asp Thr Ser Cys Ser Asp Ser Lys Thr Leu Cys Thr Gln
465                 470                 475                 480

Asp Ser Glu Ser Thr Glu Ile Pro Leu Asp Glu Gln Val Glu Glu Glu
            485                 490                 495

Ala Val Gly Glu Glu Glu Glu Ser Gln Pro Glu Ala Cys Val Ile Asp
            500                 505                 510

Asp Arg Ser Pro Asp Thr
            515

<210> SEQ ID NO 3
<211> LENGTH: 1902
<212> TYPE: DNA
<213> ORGANISM: Artificial Sequence
<220> FEATURE:
<223> OTHER INFORMATION: Description of Artificial Sequence:cDNA derived
      from mRNA from cells of rat brain hippocampal region

<400> SEQUENCE: 3
acatacatta ttcattaagc cctggagctc ggagagaaag atgcagactc ttagctcttt     60
agcctcttct tcatcacatg gatattcctt attcagaata gtcgctgaat tttgttccat    120
ttcggagttt tacaaatggc atgtgtttaa tggaagacg gctggatggg atcctaatat     180
gatgctttct tatttacgct taattaccaa aaatctttaa ctccccacac cctgaatggc    240
tttgtggaaa ctggtagaaa ttgaggtttg aagagataca catttagaa cttgctgtca     300 catatacgta tagacacata atctatcaaa aatgcctgaa gcaaactatt tattgtcagt    360 gtcttgggc tacataaagt tcaagaggat gcttaatcgg gagctcaccc acctctctga     420
aatgagtcgg tctggcaacc aggtgtcgga gtacatatca aacacgttct tagataagca    480
acatgaagta gaaattccct ctccgactca gaaggaaaaa gagaagaaga aaaggccgat    540
gtcacagatc agtggggtca agaagttgat gcacagctcc agcctgacca attcctgcat    600
cccaagattt ggggttaaaa cagagcagga agatgtcctg gccaaggaac tagaagacgt    660
gaacaagtgg ggcctccacg ttttccgaat agcggagctg tctggcaacc ggcctctgac    720
tgttatcatg cacaccattt ttcaggaacg agatttgtta aaaacgttta aaatcccagt    780
ggacactttg attacgtatc ttatgactct agaagaccat taccatgctg acgtggccta    840
tcacaacaac atccatgctg cagatgtcgt ccagtcaact catgtgctgc tctctacacc    900
cgctttggag gctgtttca ctgacttgga gattctcgcg ccattttttg ccagtgcaat     960
acatgatgtg gatcatcctg gtgtgtcaaa tcaatttctg atcaatacaa actcggaact   1020
tgccttgatg tacaacgact cctccgtctt agagaatcat catttggctg tgggctttaa   1080
gttgctccag gaagaaaact gtgacatttt ccagaatctg accaaaaagc aaagacaatc   1140
tttaaggaaa atggccattg acattgtact agcgacagac atgtcaaagc acatgaatct   1200
```

-continued

```
gctggctgat ctgaaaacaa tggttgaaac gaagaaggtg acgagctctg gcgtcctcct    1260
ccttgataac tattctgaca ggatccaggt cctccagaat atggtgcact gtgcagacct    1320
gagcaacccc acaaagccac tccagctcta ccgccagtgg acggaccgga taatggagga    1380
gttcttccgt caggggacc  gggagcgtga gcgtggcatg agataagtc  ccatgtgtga    1440 caagcacaac gcctctgtgg aaaaatcaca ggtgggcttc atagactaca ttgttcatcc    1500
actctgggag acatgggcag acctcgtaca tcccgacgcc aggacatttt ggacacttt     1560 ggaggacaat cgtgagtggt accagagcac aatcccccag agccctccc  ctgcacctga    1620 tgaccaagag gacggccgtc aggacagac  tgaaaaattc cagttcgaac taaccttaga    1680
ggaagatggc gagtcagaca ctgaaaagga cagtggaagt caagtggagg aagacactag    1740
ctgcagtgac tctaagactc tgtgcaccca agactcagag tccactgaaa ttccccttga    1800
cgagcaggtt gaagaggagg ctgtagcaga agaggaaagc cagccccaaa ctggcgtcgc    1860
agacgattgt tgtcctgaca cgtaacagtg taaaggctgt ca                       1902
```

<210> SEQ ID NO 4
<211> LENGTH: 517
<212> TYPE: PRT
<213> ORGANISM: Rattus sp.

<400> SEQUENCE: 4

```
Met Pro Glu Ala Asn Tyr Leu Leu Ser Val Ser Trp Gly Tyr Ile Lys
  1               5                  10                  15

Phe Lys Arg Met Leu Asn Arg Glu Leu Thr His Leu Ser Glu Met Ser
             20                  25                  30

Arg Ser Gly Asn Gln Val Ser Glu Tyr Ile Ser Asn Thr Phe Leu Asp
         35                  40                  45

Lys Gln His Glu Val Glu Ile Pro Ser Pro Thr Gln Lys Glu Lys Glu
     50                  55                  60

Lys Lys Lys Arg Pro Met Ser Gln Ile Ser Gly Val Lys Lys Leu Met
 65                  70                  75                  80

His Ser Ser Ser Leu Thr Asn Ser Cys Ile Pro Arg Phe Gly Val Lys
                 85                  90                  95

Thr Glu Gln Glu Asp Val Leu Ala Lys Glu Leu Glu Asp Val Asn Lys
            100                 105                 110

Trp Gly Leu His Val Phe Arg Ile Ala Glu Leu Ser Gly Asn Arg Pro
        115                 120                 125

Leu Thr Val Ile Met His Thr Ile Phe Gln Glu Arg Asp Leu Leu Lys
    130                 135                 140

Thr Phe Lys Ile Pro Val Asp Thr Leu Ile Thr Tyr Leu Met Thr Leu
145                 150                 155                 160

Glu Asp His Tyr His Ala Asp Val Ala Tyr His Asn Asn Ile His Ala
                165                 170                 175

Ala Asp Val Val Gln Ser Thr His Val Leu Leu Ser Thr Pro Ala Leu
            180                 185                 190

Glu Ala Val Phe Thr Asp Leu Glu Ile Leu Ala Ala Ile Phe Ala Ser
        195                 200                 205

Ala Ile His Asp Val Asp His Pro Gly Val Ser Asn Gln Phe Leu Ile
    210                 215                 220

Asn Thr Asn Ser Glu Leu Ala Leu Met Tyr Asn Asp Ser Ser Val Leu
225                 230                 235                 240

Glu Asn His His Leu Ala Val Gly Phe Lys Leu Leu Gln Glu Glu Asn
                245                 250                 255
```

Cys Asp Ile Phe Gln Asn Leu Thr Lys Lys Gln Arg Gln Ser Leu Arg
                260                 265                 270

Lys Met Ala Ile Asp Ile Val Leu Ala Thr Asp Met Ser Lys His Met
            275                 280                 285

Asn Leu Leu Ala Asp Leu Lys Thr Met Val Glu Thr Lys Lys Val Thr
        290                 295                 300

Ser Ser Gly Val Leu Leu Leu Asp Asn Tyr Ser Asp Arg Ile Gln Val
305                 310                 315                 320

Leu Gln Asn Met Val His Cys Ala Asp Leu Ser Asn Pro Thr Lys Pro
                325                 330                 335

Leu Gln Leu Tyr Arg Gln Trp Thr Asp Arg Ile Met Glu Glu Phe Phe
            340                 345                 350

Arg Gln Gly Asp Arg Glu Arg Glu Arg Gly Met Glu Ile Ser Pro Met
                355                 360                 365

Cys Asp Lys His Asn Ala Ser Val Glu Lys Ser Gln Val Gly Phe Ile
            370                 375                 380

Asp Tyr Ile Val His Pro Leu Trp Glu Thr Trp Ala Asp Leu Val His
385                 390                 395                 400

Pro Asp Ala Gln Asp Ile Leu Asp Thr Leu Glu Asp Asn Arg Glu Trp
                405                 410                 415

Tyr Gln Ser Thr Ile Pro Gln Ser Pro Ser Pro Ala Pro Asp Asp Gln
            420                 425                 430

Glu Asp Gly Arg Gln Gly Gln Thr Glu Lys Phe Gln Phe Glu Leu Thr
                435                 440                 445

Leu Glu Glu Asp Gly Glu Ser Asp Thr Glu Lys Asp Ser Gly Ser Gln
            450                 455                 460

Val Glu Glu Asp Thr Ser Cys Ser Asp Ser Lys Thr Leu Cys Thr Gln
465                 470                 475                 480

Asp Ser Glu Ser Thr Glu Ile Pro Leu Asp Glu Gln Val Glu Glu Glu
                485                 490                 495

Ala Val Ala Glu Glu Glu Ser Gln Pro Gln Thr Gly Val Ala Asp Asp
            500                 505                 510

Cys Cys Pro Asp Thr
        515

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:novel 15-mer
      found in cAMP phosphodiesterases from rat and human hippocampal
      cells

<400> SEQUENCE: 5

Met Pro Glu Ala Asn Tyr Leu Leu Ser Val Ser Trp Gly Tyr Ile
 1               5                  10                  15

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:Nested
      reverse primer for PCR based on rat PDE4d2 sequences in
      GenBank

<400> SEQUENCE: 6
atgcagaggc cggttgccag acagctccgc tattcgg                          37

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Nested
      reverse primer for PCR based on rat PDE4d2 sequences in
      GenBank

<400> SEQUENCE: 7
tggccaggac atcttcctgc tctgttttaa cc                              32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:Nested
      reverse primer for PCR based on rat PDE4d2 sequences in
      GenBank

<400> SEQUENCE: 8
gtcaggctgg agctgtgcat caacttcttg acc                             33

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Nested
      reverse primer for PCR based on human PDE4D sequence from
      Genbank

<400> SEQUENCE: 9
ccggttacca gacaactctg c                                          21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:Nested
      reverse primer for PCR based on human PDE4D sequence from
      Genbank

<400> SEQUENCE: 10
tggcaaggac atcttcttgt tca                                        23

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Nested
      reverse primer for PCR based on human PDE4D sequence from
      Genbank

<400> SEQUENCE: 11
gactccactg atctgagaca ttggtct                                    27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:Primer for reverse transcription of rat hippocampal mRNA

<400> SEQUENCE: 12
aggtgtgaca gcctttacac tgttacgt                                          28

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:Primer for
      reverse transcription of humant hippocampal mRNA

<400> SEQUENCE: 13
gcactgttac gtgtcaggag aa                                                22

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Rat forward
      PCR primer

<400> SEQUENCE: 14
gacacataat ctatcaaaaa tgcctgaagc                                        30

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:Rat reverse
      PCR primer

<400> SEQUENCE: 15
gacagccttt acactgttac gtgtcagg                                          28

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:human
      forward PCR primer

<400> SEQUENCE: 16
tacatataat caatcaaaaa tgcctgaagc aa                                     32

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:human
      reverse PCR primer

<400> SEQUENCE: 17
ctgttacgtg tcaggagaac gatca                                             25

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:rat forward
      primer for PCR amplification

```
<400> SEQUENCE: 18
tggaaagacg gctggatggg                                                      20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:rat reverse
      primer for PCR amplification

<400> SEQUENCE: 19
tgtagcccca agacactgac aa                                                   22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:human
      forward primer for PCR amplification

<400> SEQUENCE: 20
tgggaagacg gctggatggg                                                      20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:human
      reverse primer for PCR amplification

<400> SEQUENCE: 21
atgtagcccc aagacactga cagt                                                 24
```